United States Patent [19]

Larsson et al.

[11] 3,981,683

[45] Sept. 21, 1976

[54] TEMPERATURE RESPONSIVE STERILITY INDICATOR

[75] Inventors: Raymond P. Larsson, Denville; Robert J. Witonsky, Princeton, both of N.J.

[73] Assignee: Bio-Medical Sciences, Inc., Fairfield, N.J.

[22] Filed: Apr. 14, 1975

[21] Appl. No.: 568,149

[52] U.S. Cl. ................................ 23/253 TP; 21/2; 73/356; 73/358; 116/114 AM; 116/114 V; 116/114 Y
[51] Int. Cl.² ................ G01N 31/22; G01K 11/06; G01K 11/12
[58] Field of Search ............ 23/253 TP; 73/356, 358; 21/2; 116/114 AM, 114 V, 114 Y

[56] References Cited
UNITED STATES PATENTS

| | | | |
|---|---|---|---|
| 2,799,167 | 7/1957 | Loconti | 73/356 |
| 2,889,799 | 6/1959 | Korpman | 23/253 TP X |
| 3,002,385 | 10/1961 | Wahl et al. | 23/253 TP X |
| 3,046,786 | 7/1962 | Tessem | 73/356 |
| 3,082,624 | 3/1963 | Renier | 73/356 |
| 3,420,205 | 1/1969 | Morison | 23/253 TP X |

*Primary Examiner*—Norman Yudkoff
*Assistant Examiner*—Dale Lovercheck
*Attorney, Agent, or Firm*—Anthony Lagani, Jr.

[57] ABSTRACT

A sterility indicator comprising a backing strip of a dimensionally stable material e.g. aluminum foil having mounted thereon an organic compound containing oxygen or nitrogen in intimate contact with a wicking means and a cover strip bonded to the backing strip overlaying the organic compound and wicking means. The cover strip is a polymeric rate controlling film which permits water vapor to pass through at a rate sufficient to make the device operative at a temperature to be monitored.

17 Claims, 3 Drawing Figures

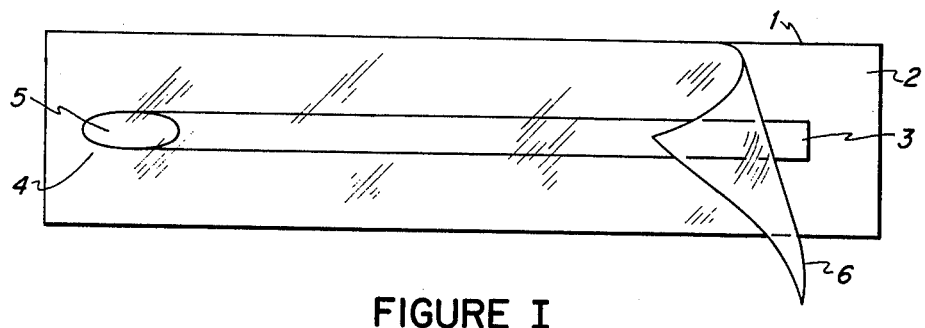
FIGURE I
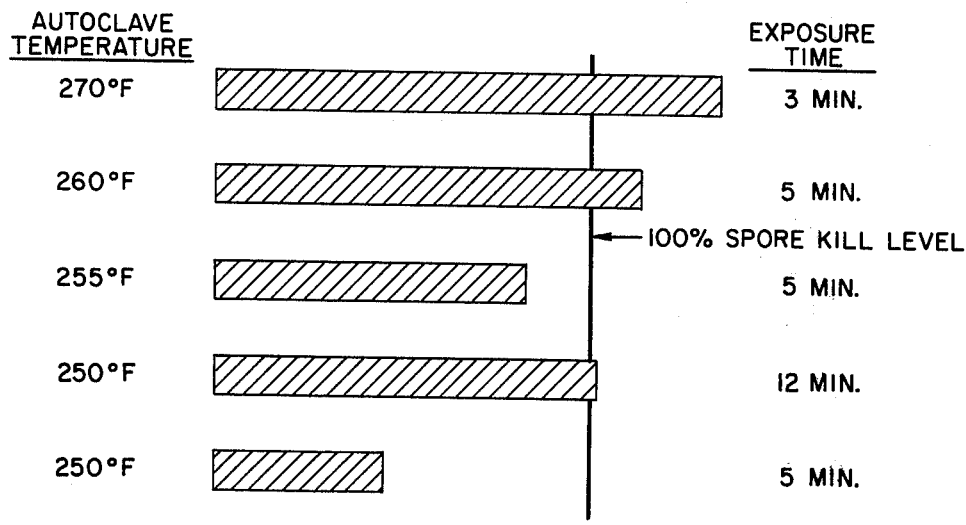
FIGURE II
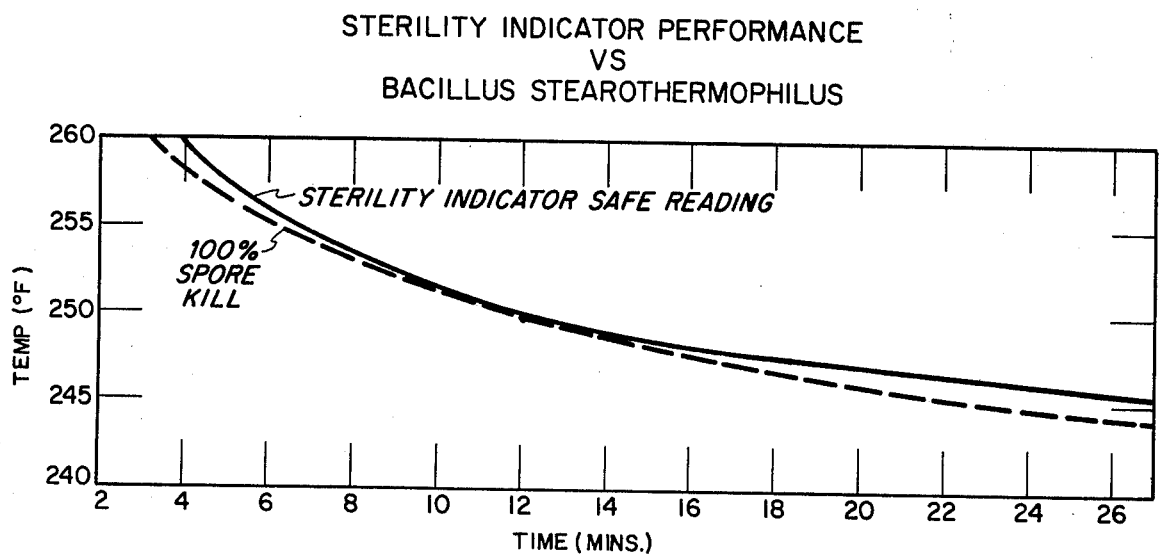
FIGURE III

TEMPERATURE RESPONSIVE STERILITY INDICATOR

BACKGROUND OF INVENTION

It is well known in the art that heat will destroy microorganisms. The presence of moisture accelerates this destruction by denaturing or coagulation of the proteins making up the microorganisms. Most microorganisms contain sufficient water so that moderate heat alone, e.g. 80°–100°C., will destroy the microorganism. Many bacterial spores, on the other hand, contain substantially no water and require elevated temperatures in excess of 150°C. for their destruction where dry heat is used. Hence, the destruction of such organisms is generally carried out in the presence of steam in autoclaves.

Such steam sterilization is generally carried out at temperatures of about 250°F. for at least 12 to 15 minutes or for shorter times at higher temperatures e.g. 270°F. Often, to insure a sufficient safety margin, times as long as 30 minutes are used. Such long sterilization times give the operator a greater degree of confidence that steam has penetrated throughout the autoclave and among all of its contents. However, such long heat cycles are disadvantageous from the standpoint of economy of time, energy consumption, and severe shortening of the useful life of the sterilized material, e.g., fabric gowns, drapes, muslim products etc.

From time to time attempts have been made to develop sterilization indicators which permit quality control of sterilization with the confidence that all microorganisms have been destroyed. Presently the most satisfactory method is the use of spore strips. Spores which are particularly difficult to destroy are selected as the control standard, e.g., *Bacillus Subtilis var. Niger* and *Bacillus Stearothermophilus*. The spore strip is placed in the autoclave with the materials to be sterilized. At the end of the sterilization cycle, the spore strip is studied to determine whether it is possible to grow organisms in a suitable culture medium. Failure of the spores to reproduce indicates death of spores; and hence, adequate sterilization.

Although this control technique is accurate, it suffers from several inherent disadvantages, (1) excessive cost (2) delay between processing and control data (3) batch to batch variation of the spores and (4) heat resistance of spores decreases with storage time.

Several attempts have been made to devise chemical type sterility indicators. The crudest variety is a product known as Temp-Tube, see for example, U.S. Pat. Nos. 3,313,266; 3,341,238; and 3,652,249. The device consists of nothing more than a sealed tube containing a compound with a melting point which corresponds to the sterilization temperature. The device is capable of doing no more than indicating whether or not the autoclave was held at a temperature above or below the melting point for a period of time once the melting point is reached. Hence, the device only indicates that the desired melting point temperature was reached for a period of time sufficient to melt the indicator.

Other sterility indicators rely on a temperature accelerated chemical reaction to cause color change in an indicator. Though some of these devices purport to be operative at more than one temperature/time condition, they suffer from the disadvantage that they do not match the spore kill temperature/time relationships. The thermal resistance of spores of a particular species at any temperature is characterized by its temperature coefficient. The symbol $Q_{10}$ is used to designate the temperature coefficient over a range of 10°C. It means the ratio of the death rate constant at a particular temperature to the death rate constant at a temperature 10°C. lower. Generally, the measurements are made for a fixed time interval, e.g., 9 minutes. If the constants at any two temperatures, $t_1$, and a temperature 10°C. higher, $t_2$, are known, then $Q_{10}$ may be calculated from the equation:

$$\log Q_{10} = \frac{10}{t_2 - t_1} \log \frac{K_2}{K_1}$$

wherein $t_1$ and $t_2$ are as defined and $K_1$ and $K_2$ are the respective death rate constants. Spores generally exhibit a $Q_{10}$ value of about 10. Therefore, it is desirable to have a sterility indicator which will, in a sense, mimic spore kill. To do so, the ratio of the effect of temperature as a function of time on a measurement taken at one temperature as compared to the same measurement at another temperature 10°C. lower should also be 10. To be useful as a sterility indicator, this relationship must also be dependent on the presence of moisture, since the spore kill time/temperature relationship is vastly different in the dry or wet state. In the absence of moisture spore kill at 250°–270°F. is negligible, but in the presence of steam spore kill is virtually complete for the most resistant strains at these temperatures in about 12–2 minutes.

SUMMARY OF INVENTION

It has surprisingly been found that a suitable sterility indicator which is dependent on the presence of moisture can be constructed using an organic compound having a melting point slightly higher than the sterility temperature to be monitored. A pellet of the compound is placed on a backing in contact with a wick and covered with a transparent polymeric covering which protects the compound and wick from direct contact with steam, as well as maintains the integrity of the device.

It is important to the function of the sterility indicator that steam may diffuse through the cover film. Additionally, the melting point of the organic compound must be depressed by the absorption of moisture into the pellet.

The cover film functions to control the rate of water vapor transmissions into the organic compound. Proper selection of organic compound and polymeric cover film determine the operative temperature as well as the time/temperature coefficient for the device.

Illustrative non-limiting examples of specific types of functional groups which when included in the structure of a compound results in useful organic compounds in the practice of this invention are aldehyde, carbonyl, ester keto, ether, hydroxy amino, amide, carboxy etc. Generally the organic compound should contain either oxygen or nitrogen.

BRIEF DESCRIPTION OF DRAWINGS

FIG. I shows structural configuration of the sterility indicator.

FIG. II is a bar graph representation of the integrating effect of the sterility indicator.

FIG. III is a graphical comparison of the time/temperature coefficient of the indicator of this invention and spore kill.

DETAILED DESCRIPTION

This invention relates to a sterility indicator. More specifically, it relates to a sterility indicator capable of giving a visual response to the integrated time/temperature exposure of a system to moist heat.

FIG. 1 shows a typical structure for the sterility indicator of this invention. A backing strip, 1, is coated with a thin layer of adhesive, 2, a wicking means, 3, is positioned on the backing strip with one end in communication with a pocket, 4, embossed into the backing strip, 1. A pellet of organic compound, 5, is inserted into the pocket, 4, and in communication with the wicking means, 3. A cover strip, 6, is then pressed in place on top of the device, the cover strip, 6, being adhesively bonded in place.

The composition of the backing strip is not critical. It, however, must be dimensionally stable at the process temperature being monitored. Although polymeric materials can be used, in order that they have substantial dimensional stability, they must be of a heavier guage than desired from the standpoint of economics and overall thickness of the device. Additionally, the embossing of the pocket requires the application of heat and pressure. Hence, the preferred backing strip is metal foil, e.g., aluminum foil. Though the thickness of the foil is not critical, it is preferred that foil of about 1 to 5 mils is used e.g. 3 mils. Any of the polymers used as the cover strip can be used as the material of construction of the backing strip. However, the backing strip in that event is preferable at least about 10 mils in thickness, more preferably about 20 to 30 mils. The term "dimensionally stable" as used in the specifications and claims with reference to the backing strip means that the backing strip will not change dimensions by shrinkage, wrinkling etc. as a result of exposure to process temperatures.

The wicking means may be any suitable material through which the organic compound can migrate by capillary action. The preferred wicking means is a paper strip. Other such wicking means such as nonwoven polymeric fabrics and inorganic fibrous compositions may be used.

The dimensions of the wicking means is not critical. However, its dimensions (thickness and width) will affect the rate of wicking and determine the quantity of organic compound required to result in a suitable scale length. Hence, from an economic standpoint the wicking means should be as thin as practical. A suitable width for the wicking means is about 3/16 to about ¼ of an inch.

Illustrative of the wicking means which may be used are Whatman No. 1 filter paper, Whatman No. 114 filter paper, supported microcrystalline cellulose (TLC plate), supported aluminum oxide, and supported silica gel.

The cover strip is a rate controlling film which permits moisture (gaseous) to pass through at a rate sufficient to depress the melting point of the organic compound to the sterilization temperature to be monitored. The necessary vapor transmission rate will of course depend on the operating temperature and the organic compound selected.

It is possible to make precise determinations of vapor transmission rate as a function of temperature for various films and the effect of water vapor on melting point depression of various compounds. These data may then be used to select combinations of cover strip vapor barrier and organic compound suitable for a particular temperature to be monitored. Such a fundamental approach to component selection is neither necessary nor desirable, since it is only approximate, and an actual trial must be made in any event. Hence, an Edisonian approach results in the most rapid method of selection.

In selecting the rate controlling cover strip, it is of course necessary that the polymeric composition of the cover strip is not subject to attack by the organic compound. For example, mylar (ethylene glycol terephthalic acid ester) may not be used where the organic compound is a hydroxy containing aromatic compound, e.g., alkyl substituted phenols. Illustrative examples of suitable cover strip material are mylar, polyproplene, polyethylene, polystyrene, polymethylmethacrylate, etc. Of course it will be obvious to those skilled in the art that the polymers may not be used above their softening point. The cover strip should be transparent and preferable clear. A preferred cover strip material is polypropylene since it has a high softening point and is relatively inert to most chemical compounds. Additionally, it has an acceptable water vapor transmission rate at temperatures about 250°F., the temperature at which sterilization processes are usually carried out.

The thickness of the cover strip film will of course effect the vapor transmission rate. Preferably the film is about 0.75 to about 3 mils, more preferably about 1 to about 2 mils, e.g., 1.25 mils.

The term "rate controlling" when used in the specification and claim with respect to the cover strip means that the cover strip controls the water vapor transmission rate by virtue of its permeability to water vapor at the temperature to be monitored. No effort is made to determine the actual vapor transmission rate or in any other way to control the vapor transmission rate.

In selecting a system for a sterility indicator, the first step is to select a cover strip and backing strip. As a first choice aluminum foil is selected as the backing strip and polypropylene is selected as the cover strip. The wicking means is, typically, conventional filter paper, e.g., Whatman 1 filter paper. It then is only necessary to select a suitable organic compound.

In selecting the organic compound for the purposes of this invention, it must be a compound in which water has at least a slight degree of solubility. The compound selected should have a normal melting point about 5° to about 50°F. greater than the sterilization temperature to be monitored; more preferably, about 8° to about 40°F; most preferably, about 10° to about 30°F. greater than the temperature to be monitored, e.g., 20°F. greater.

That water be soluble in the organic compound to a slight extent is essential to the operation of the device of this invention. Not wishing to be bound by theory, it is believed that the water acts as a melting point depressant. The object in selecting an organic compound having a melting point higher than the temperature to be monitored but capable of having its melting point depressed by the absorption of water is to insure that the device will be inoperative in the absence of water vapor at the control temperature. The term "control temperature" as used in the specification and claims means the temperature to be monitored for the process in question, e.g., sterilization, pasteurization, etc.

Though it is possible to determine the actual degree of water solubility in the organic compound, it is not essential. In addition to having the specified melting point as described above, the compound should contain functional groups which will result in a degree of water solubility. Illustrative of the functional groups which the organic compound must contain are aldehyde, carbonyl, ester, keto, ether, hydroxy, amino, amide, carboxy, phosphate, phosphonate sulfones, sulfate, sulfonate, etc. Structurally these functional groups are:

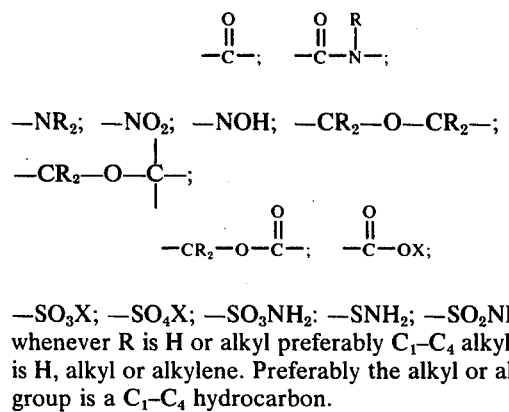

$-SO_3X$; $-SO_4X$; $-SO_3NH_2$; $-SNH_2$; $-SO_2NH_2$ whenever R is H or alkyl preferably $C_1-C_4$ alkyl and X is H, alkyl or alkylene. Preferably the alkyl or alkylene group is a $C_1-C_4$ hydrocarbon.

Hence, the organic compounds of this invention are heterogenous compounds which must contain oxygen or nitrogen in the structure. In addition to oxygen and nitrogen, other non-reactive substituents may be included such as chlorine, sulfur, phosphorus, etc.

Hence, the term "organic compound" as used in the specification and claims means an organic compound containing in its structure at least one oxygen or nitrogen atom as well as carbon atoms. As stated above, other atoms can be included in the structure. Illustrative examples of organic compounds suitable for use in the practice of this invention are 2-chloroacetamide, ethoxy benzamide, benzoic acid, diphenyl succinate, dichlorophenol, dimethyl phenol, benzamide, urea, 1,4 dihydroxybenzophenone, hydroquinone, dioxime, ethylene ester of toluene sulfonic acid, aslicylamide, and salicylic acid.

It is preferred that the cover strip be adhered to the backing strip with an adhesive. Heat sealing, however, can be used instead of adhesives. Any adhesive for bonding polymers to metal or polymers to polymers can be used. The adhesive of course must be resistant to attack by the organic compound. The preferred adhesives are silicone adhesives, e.g., General Electric Company's Sil Grip 574. The term "bonding" or "bonded" as used in the specification and claims includes both heat sealing and adhesive lamination of the backing strip to the cover strip. In preparing sterility indicator for a given application, as a first approximation, aluminum foil is used as the backing strip, and polypropylene film is used as the rate controlling cover strip. An organic compound having a normal melting point about 20-30°F. above the control point is selected. A pocket or depression is embossed into the backing strip and a pellet of the organic compound is placed in the pocket. The wicking means is aligned to the backing strip with a portion of one end under the pellet. For convenience of preparation the backing strip is first coated with an adhesive material. Thus the pellet and wicking means will remain in place. The cover strip is then pressed in place.

The system is tested by placing it into a steam autoclave held at the control temperature and at the corresponding saturated steam pressure. After about twelve minutes the device is removed from the autoclave and observed. No additional wicking should occur after removal from the autoclave. Not wishing to be bound by theory, it is believed additional wicking after removal from the autoclave or at temperatures below the control temperature are the result of supercooling or the formation of a supersaturated solution of water and organic compound which permits wicking below the control temperature.

If no wicking occurs after dropping the temperature and the length of wicking of organic compound along the wicking means is satisfactory to give an acceptable scale for the desired application, the screening test is continued.

A similar test specimen is prepared and tested at about 5°F. below the control temperature no wicking should occur. Additional tests should be conducted about 5°F. above and below the control temperature to determine the $Q_{10}$ value for the compound selected. Where it is desired to have a $Q_{10}$ which matches a particular process, e.g., spore kill, may be necessary to repeat the process with other organic compounds.

It has been found that the $Q_{10}$ value is effected by the nature of the cover strip. For example whereas a sterility indicator which uses polypropylene as the rate controlling cover strip and ethoxy benzamide as the organic compound as a $Q_{10}$ of about 18. When mylar (polyethyleneglycol terephthalic acid ester) is used as the cover strip the $Q_{10}$ is about 4–5.

Since most organic compounds are colorless, it is desirable to include a dye in the organic compound to make it visible on the wicking means. Alternately, the dye may be applied to the initial portion (nearest the pellet of organic compound) of the wicking means. As the organic compound moves along the wick it picks up dyestuff and carries it along the wicking means. Any suitable dye which is soluble in the organic compound may be used. Illustrative examples of such dyes are: methylene blue, crystal violet, malachite green, brilliant green, methyl violet and methyl green.

Where the organic compound is acid or basic it may be made visible by presaturating the wicking means with a suitable pH sensitive dye. As the organic compound wicks along the wicking means it will cause a color response change in the pH sensitve dye. Illustrative examples of such pH sensitive dyes are phenolphthalein, xylenol blue, Nile blue A, m-cresol purple, bromocresol green, thymol blue, bromophenol blue, alizarin, bromphenol red, methyl red, brilliant yellow, phenol red, etc.

EXAMPLE I

Sterility Indicators were prepared using aluminum foil as the backing strip and Whatman No. 1 filter paper as the wicking means. The wick was about ¼ inch × 4 inches. Pellets of organic compound were prepared using about 50 mg of compound. General Electric Companys' silicone adhesive Sil Grip 574 was used to bond the rate controlling cover strip to the backing, the adhesive being applied to the backing only.

Each device was tested in a steam autoclave for a fixed period of time at various temperatures. The conditions and results are tabulated in Table I.

TABLE I

Wicking Distance As a Function of Time and Temperature

| Organic Compound | Normal Melting Point (°F) | Cover Strip Composition and Thickness | Time (min) | Autoclave Temperature (°F) | Wicking Distance (mm) | Approximate $Q_{10}$ |
|---|---|---|---|---|---|---|
| Urea | 271 | mylar (1 mil) | 10 | 240 | 14 | |
| | | | 10 | 250 | 22 | 2.3 |
| Succinimide | 257 | mylar (1 mil) | 10 | 240 | 14 | |
| | | | 10 | 250 | 22 | 2.3 |
| Benzamide | 266 | mylar (2 mil) | 10 | 240 | 23 | |
| | | | 10 | 250 | 26 | 1.3 |
| Dihydroxy-benzophenone | 300 | Polyproplene (1 ¼ mil) | 10 | 245 | 0 | |
| | | | 10 | 250 | 3 | |
| | | | 10 | 260 | 16.5 | 22 |
| Cinnamic Acid | 273 | Polyproplene (1 ¼ mil) | 10 | 245 | 0 | |
| | | | 10 | 250 | 10 | |
| | | | 15 | 240 | 11 | 5.7 |
| | | | 15 | 245 | 17 | |
| | | | 15 | 250 | 29 | |
| | | mylar (2 mil) | 15 | 245 | 10 | |
| | | | 15 | 250 | 16 | 5.4 |
| Ethoxy benzamide | 271 | Polyproplene (1 ¼ mil) | 10 | 240 | 18 | |
| | | | 10 | 245 | 21 | |
| | | | 10 | 250 | 48 | |
| | | | 15 | 245 | 33 | |
| | | | 15 | 250 | 71 | 18 |
| | | | 25 | 240 | 24 | |
| | | | 25 | 245 | 48 | |
| | | | 5 | 250 | 29 | |
| | | | 5 | 255 | 52 | |
| | | | 5 | 260 | 68 | |
| | | | 3 | 270 | 83 | |
| | | mylar (1 mil) | 10 | 245 | 42 | |
| | | | 10 | 250 | 55 | 2.6 |

The data presented in Table I shows that both the thickness of cover strip and its composition will effect the $Q_{10}$ value obtained using the same organic compound.

EXAMPLE 2

Data was obtained on samples prepared in the manner of Example I using ethoxy benzamide as the organic compound and 1 ¼ mil polyproplene as the cover strip. The results for various time exposures at different temperatures are shown in terms of a bar graph in FIG. II. The length of the bar represents the wicking distance for the time and temperature shown. The vertical line shows the wicking distance required for 100% spore kill in a steam sterilization process. The data presented demonstrates that the device of this invention is capable of intergrating the time/temperature exposure to a saturated steam atmosphere.

EXAMPLE 3

The device of Example 2 was subjected to temperatures below 270°F, the normal melting point of ethoxy benzamide using an oil bath. No wicking occurred. The same experiment was repeated at temperatures as high as 275°F. Wicking was very slow as compared to in a steam atmosphere. These results show that the device of this invention is inoperative at normal sterilization temperatures in the absence of saturated steam. Under such conditions, therefore, the device would indicate inadequate sterilization.

FIG. 3 shows a comparison of the device of this invention as described in Example 3 against spore strips as a sterility indicator. It is noted that the time/temperature coefficient of the sterility indicator of this invention mimics spore kill. Furthermore, for a given temperature the safe reading for the recommended sterilization is always slightly more than the time required for spore kill. Hence, the device will fail safe if exposure times are insufficient.

Although the invention is described in terms of a sterility indicator, it will be obvious to those skilled in the art that it will have other applications such as pasturization e.g. beer pasturization at 140°F.

What is claimed is:

1. A sterility indicator device for use in a steam autoclave comprising:
   a. a backing strip
   b. an organic compound having a normal melting point which is greater than a predetermined control temperature said melting point being depressed below said control temperature by the absorption of water into the organic compound when said organic-compound is exposed to saturated water vapor at the control temperature, said control temperature being below the normal melting point of the organic compound, said compound being mounted on said backing strip.
   c. a wicking means having one end of said wicking means in intimate contact with said compound, said wicking means extending away from said compound and being mounted on said backing strip; and
   d. a water vapor transmission rate controlling cover strip overlayer covering said compound and wicking means said cover strip being bonded to said backing strip and being permeable to water vapor and having a water permeability coefficient at the control temperature such that sufficient water vapor will permeate the cover strip to reduce the melting point of the organic compound from its normal melting point to the control temperature; said device being inoperative at the predetermined control temperature in the absence of saturated steam and displaying a visual response of the integrated time/temperature exposure of a system to moist heat.

2. The indicator according to claim 1 wherein the backing strip is aluminum foil.

3. The indicator according to claim 1 wherein the organic compound selected from the group consisting of ethoxy benzamide, 2-chloro acetamide, dihydroxy benzaphenone and benzoic acid.

4. The indicator according to claim 1 wherein the cover strip is a film of material selected from the group consisting of mylar, polypropylene, and cellulose acetate.

5. The indicator according to claim 1 wherein the organic compound is ethoxy benzamide, the cover strip is polypropylene film and the backing strip is aluminum foil.

6. The indicator according to claim 1 wherein the wicking means is paper.

7. The indicator according to claim 1 wherein a dye is incorporated into the organic compound.

8. The indicator according to claim 7 wherein the dye is selected from the group consisting of methylene blue, malachite green and brilliant green.

9. The indicator according to claim 5 wherein a dye is incorporated into the ethoxy benzamide.

10. The indicator according to claim 9 wherein the dye is methylene blue.

11. The indicator of claim 1 wherein the wicking means is impregnated with a dye at an end of said wicking means near the organic compound.

12. The indicator of claim 11 wherein the dye is methylene blue.

13. The indicator of claim 1 wherein the wicking means is adhesively bonded to the backing strip.

14. The indicator of claim 1 wherein the cover strip is adhesively bonded to the backing strip.

15. The indicator of claim 14 wherein the adhesive is a silicone adhesive.

16. The indicator according to claim 1 wherein the organic compound is an acidic compound and the wicking means is presaturated with a pH sensitive dye.

17. The indicator of claim 1 wherein the organic compound is a basic compound and the wicking means is presaturated with a suitable pH sensitive dye.

* * * * *

UNITED STATES PATENT AND TRADEMARK OFFICE
CERTIFICATE OF CORRECTION

PATENT NO. : B1 3,981,683
DATED : July 14, 1992
INVENTOR(S) : Larsson et al

It is certified that error appears in the above-indentified patent and that said Letters Patent is hereby corrected as shown below:

On the title page, item [56] References Cited, add the following patents:

--3,324,723  6/1967  Ritchie................ 73/358
  3,479,877  11/1969 Allen.................. 73/358

At column 5, line 44, after "acid", cancel "aslicylamide" and insert --salicylamide--.

Signed and Sealed this

Twenty-first Day of December, 1993

Attest:

BRUCE LEHMAN

Attesting Officer

Commissioner of Patents and Trademarks

REEXAMINATION CERTIFICATE (1741st)
United States Patent [19]
Larsson et al.

[11] B1 3,981,683
[45] Certificate Issued    Jul. 14, 1992

[54] TEMPERATURE RESPONSIVE STERILITY INDICATOR

[76] Inventors: Raymond P. Larsson, Denville; Robert J. Witonsky, Princeton, both of N.J.

Reexamination Request:
No. 90/002,402, Aug. 15, 1991

Reexamination Certificate for:
Patent No.: 3,981,683
Issued: Sep. 21, 1976
Appl. No.: 568,149
Filed: Apr. 14, 1975

[51] Int. Cl.⁵ .................. G01N 31/22; G01K 11/06; G01K 11/12
[52] U.S. Cl. ............................ 422/57; 116/207; 116/219; 422/58; 374/106
[58] Field of Search ..................... 422/56–58, 422/61; 436/1; 435/31; 374/102–107; 116/216, 217, 219, 207

[56] References Cited
U.S. PATENT DOCUMENTS

| | | |
|---|---|---|
| 161,118 | 3/1875 | Halvorson . |
| 197,902 | 12/1877 | Scott . |
| 1,000,673 | 8/1911 | Diack . |
| 1,191,572 | 7/1916 | Davis . |
| 1,238,123 | 8/1917 | Freeman . |
| 1,426,569 | 8/1922 | Ingram . |
| 1,441,307 | 1/1923 | Swanberg . |
| 1,535,536 | 4/1925 | MacDonald . |
| 1,558,153 | 10/1925 | Ferkel . |
| 1,676,536 | 7/1928 | Ferkel . |
| 1,703,880 | 5/1929 | Gordon . |
| 1,788,104 | 1/1931 | Hargreaves . |
| 1,843,234 | 2/1932 | Karnes et al. . |
| 1,894,015 | 1/1933 | Berstein . |
| 1,917,048 | 7/1933 | Midgley . |
| 1,951,650 | 3/1934 | Diack . |
| 2,046,863 | 7/1936 | Allphin ............................ 73/32 |
| 2,049,867 | 8/1936 | Richards ........................... 40/2 |
| 2,188,144 | 5/1938 | Berman et al. .................. 73/356 |
| 2,195,395 | 4/1940 | Chapman .......................... 23/5 |
| 2,222,067 | 11/1940 | Chaney et al. ............... 116/114 |
| 2,269,038 | 1/1942 | Perry ............................ 116/114 |
| 2,277,278 | 3/1942 | Triplett ........................ 99/192 |
| 2,278,749 | 2/1957 | Beckett et al. ............... 116/114 |
| 2,308,087 | 1/1943 | Lappala ........................ 73/356 |
| 2,335,999 | 12/1943 | Diack ........................... 73/358 |
| 2,337,534 | 12/1943 | Barber ............................ 35/1 |
| 2,379,459 | 7/1945 | Schreiber et al. ............ 73/358 |
| 2,460,215 | 1/1949 | Chase ........................... 99/192 |
| 2,490,933 | 12/1949 | Tornquist et al. ............ 73/358 |
| 2,552,477 | 5/1951 | Cole ............................ 73/193 |
| 2,560,537 | 7/1951 | Anderson ....................... 99/192 |
| 2,567,445 | 9/1951 | Parker ......................... 23/230 |
| 2,579,738 | 12/1951 | Hargreaves .................... 73/358 |
| 2,606,654 | 8/1952 | Davis et al. .................. 206/47 |
| 2,614,430 | 10/1952 | Ballard et al. ................ 73/358 |
| 2,677,278 | 5/1954 | Smith et al. .................. 73/358 |
| 2,708,896 | 5/1955 | Smith et al. ................. 116/114 |
| 2,716,065 | 8/1955 | Beckett et al. ................ 99/192 |
| 2,798,855 | 7/1957 | Hainsworth .................... 252/408 |
| 2,798,856 | 7/1957 | Hainsworth .................... 252/408 |

(List continued on next page.)

FOREIGN PATENT DOCUMENTS 141266   3/1949   Australia .
407208   8/1968   Australia .

(List continued on next page.)

OTHER PUBLICATIONS

A. Hoyt, "Studies on Rubber Glove Sterilization and the Use of Sterility Indicators", 19 J. Lab. Clin. Med. at 382–390 (1934).

(List continued on next page.)

*Primary Examiner*—Jill Johnston

[57] ABSTRACT

A sterility indicator comprising a backing strip of a dimensionally stable material e.g. aluminum foil having mounted thereon an organic compound containing oxygen or nitrogen in intimate contact with a wicking means and a cover strip bonded to the backing strip overlaying the organic compound and wicking means. The cover strip is a polymeric rate controlling film which permits water vapor to pass through at a rate sufficient to make the device operative at a temperature to be monitored.

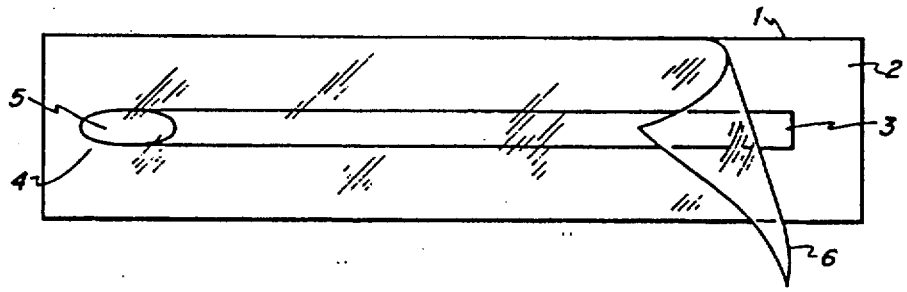

U.S. PATENT DOCUMENTS

| | | | |
|---|---|---|---|
| 2,799,167 | 7/1957 | Loconti | 73/356 |
| 2,826,073 | 3/1958 | Huyck et al. | 73/356 |
| 2,847,067 | 8/1958 | Brewer | 161/15 |
| 2,850,393 | 9/1958 | Romito | 99/192 |
| 2,854,384 | 9/1958 | Beakley | 195/54 |
| 2,889,799 | 6/1959 | Korpman | 116/114 |
| 2,915,405 | 12/1959 | Hammond et al. | 99/192 |
| 2,918,893 | 12/1959 | Norton | 116/114 |
| 2,928,791 | 3/1960 | Loconti | 252/408 |
| 2,932,971 | 4/1960 | Moore et al. | 73/356 |
| 2,951,764 | 9/1960 | Chase | 99/192 |
| 2,971,852 | 2/1961 | Schulein | 99/192 |
| 2,998,306 | 8/1961 | Huyck et al. | 23/254 |
| 3,002,385 | 10/1961 | Wahl et al. | 73/356 |
| 3,018,611 | 1/1962 | Biritz | 58/1 |
| 3,046,786 | 7/1962 | Tessem | 73/356 |
| 3,047,405 | 7/1962 | Lanier | 99/192 |
| 3,055,759 | 9/1962 | Busby et al. | 99/192 |
| 3,059,474 | 10/1962 | Keller et al. | 73/358 |
| 3,065,083 | 11/1962 | Gessler | 99/192 |
| 3,067,015 | 12/1962 | Lawdermilt | 23/253 |
| 3,078,182 | 2/1963 | Crone, Jr. et al. | 117/68.5 |
| 3,082,624 | 3/1963 | Renier | 73/356 |
| 3,093,242 | 6/1963 | Huyck et al. | 206/47 |
| 3,098,751 | 7/1963 | Huyck et al. | 106/20 |
| 3,114,349 | 12/1963 | Schuman | 116/114 |
| 3,118,774 | 1/1964 | Davidson et al. | 99/192 |
| 3,205,158 | 9/1965 | Renier | 204/195 |
| 3,242,733 | 3/1966 | Johnson | 73/344 |
| 3,243,303 | 3/1966 | Johnson | 99/192 |
| 3,288,718 | 11/1966 | Carumpalos | . |
| 3,311,084 | 3/1967 | Edenbaum | 116/114 |
| 3,313,266 | 4/1967 | Kelson | 116/114 |
| 3,324,723 | 6/1967 | Ritchie | 73/358 |
| 3,341,238 | 9/1967 | White | 289/1.5 |
| 3,344,670 | 10/1967 | Olsen et al. | 73/356 |
| 3,352,794 | 11/1967 | Abdo | 252/408 |
| 3,360,337 | 12/1967 | Edenbaum et al. | . |
| 3,360,338 | 12/1967 | Edenbaum | . |
| 3,360,339 | 12/1967 | Edenbaum | . |
| 3,386,807 | 6/1968 | Edenbaum | . |
| 3,399,284 | 8/1968 | Morison | 200/61.05 |
| 3,414,415 | 12/1968 | Broad | 99/192 |
| 3,420,205 | 1/1969 | Morison | 116/114 |
| 3,430,491 | 3/1969 | Gignilliat | 73/358 |
| 3,437,070 | 4/1969 | Campbell | 116/114 |

FOREIGN PATENT DOCUMENTS

| | | |
|---|---|---|
| 425236 | 7/1970 | Australia . |
| 625917 | 12/1962 | Belgium . |
| 498481 | 12/1953 | Canada . |
| 823264 | 12/1965 | Canada . |
| 917548 | 12/1972 | Canada . |
| 976741 | 10/1975 | Canada . |
| 994221 | 8/1976 | Canada . |
| 2134314 | 7/1971 | Fed. Rep. of Germany . |
| 1461252 | 10/1966 | France . |
| 45-17039 | 2/1967 | Japan . |
| 49-20385 | 4/1973 | Japan . |
| 425276 | 5/1967 | Switzerland . |
| 551783 | 3/1943 | United Kingdom . |
| 602753 | 6/1948 | United Kingdom . |
| 647379 | 6/1950 | United Kingdom . |
| 889573 | 2/1962 | United Kingdom . |
| 910520 | 11/1962 | United Kingdom . |
| 1026950 | 4/1966 | United Kingdom . |
| 1027417 | 4/1966 | United Kingdom . |
| 1132334 | 10/1968 | United Kingdom . |
| 1212859 | 11/1970 | United Kingdom . |
| 1215891 | 12/1970 | United Kingdom . |
| 1360861 | 7/1974 | United Kingdom . |
| 1367703 | 9/1974 | United Kingdom . |
| 1415782 | 11/1975 | United Kingdom . |

OTHER PUBLICATIONS

C. W. Walter, "An Evaluation of Sterility Indicators", 2 Surgery at 585-589 (1937).

E. E. Ecker, "Sterilization Based on Temperature Attained and Time Ration", 48 Modern Hospital at 86-90 (1937).

W. B. Underwood, "Methods of Testing", A Textbook of Sterilization at 98-105 (1941).

O. Rahn, "Physical Methods of Sterilization of Microorganisms", 1 Bacteriological Reviews at 1-47 (1945).

Ernest O. McCulloch, "Bacteriological and Surgical Sterilization by Heat", Disinfection and Sterilization at 69-105 (1945).

Carl W. Walter, "Sterilization by Dry Heat", The Aseptic Treatment of Wounds at 92-96 (1948).

L. F. Ortenzio, L. S. Stuart and J. L. Friedl, "The Resistance of Bacterial Spores to Constant Boiling Hydrochloric Acid", 36 Journal of the Assoc. of Official Agricultural Chemists at 480-485 (1953).

J. H. Brewer and C. B. McLaughlin, "A Device for Determining Time and Temperature of Sterilization in the Autoclave or Hot-Air Oven", 120 Science at 501-502 (1954).

Lawrence P. Garrod, "Sterilization Methods", British Medical journal at 350-351 (1955).

J. W. Howie and Morag C. Trimbury, "Laboratory Tests of Operating-Theatre Sterilizers", Lancet at 669-673 (1956).

A. C. Scott and M. B. Glasg, "Gravity Air-Displacement Pressure Steam Sterilizers", Lancet at 633-637 (1957).

V. G. Adler and W. A. Gillespie, "The Sterilization of Dressings", 10, J. Clin. Path. at 299-306 (1957).

(List continued on next page.)

OTHER PUBLICATIONS

J. C. Kelsey, "The Testing of Sterilizers", 1 Lancet at 306–309 (1958).

E. M. Darmady, K. E. A. Hughes and J. D. Jones, "Thermal Death–Time of Spores in Dray Heat", 2 Lancet at 766–769 (1958).

*Diack Sterilizer Controls*, "Smith & Underwood" Advertisement for Diack Control, 92 Modern Hospital at 8 (1959).

*Inform Controls*, "Smith & Underwood" advertisement for Inform Controls, 93 Modern Hospital at 6 (1959).

*Weckink Control*, "Edward Weck & Company" advertisement for Weck Catheter Sterilizing Papers, 93 Modern Hospital at 182 (1959).

J. W. Howie, "Sterilization by Steam Under Increased Pressure", 1 Lancet at 425–435 (1959).

*Scotch Hospital Tapes*, "Minnesota Mining and Manufacturing Company" advertisement for Scotch Brand Hospital Tapes by Minnesota Mining And Manufacturing Company, 92 Modern Hospital at 113 (1959).

*ATI Steriline Bags*, "Aseptic–Thermo Indicator Company" advertisement for A.T.I. sterilization aids including Steam–Clox Indicators, Steriline Bags and Tubing, 92 Modern Hospital at 142 (1959).

G. R. Wilkinson, "The Correlation of Oven Testing and Field Storage of Pharmaceutical Products", 35 Pharm. Acta.. Helv. at 327–332 (1959).

*ATI Steam–Clox*, "Aseptic Thermo Indicator Company" advertisement for ATI Steam–Clox Control", 94 Modern Hospital at 184 (1960).

*Pro–Tex–Mor Medical Division*, "Central States Paper & Bag Co.", 38 Hospital Topics at 115 (1960).

*ATI Steriline Bags*, "Aseptic–Thermo Indicator Company ", advertisement for Steriline Bags, 95 Modern Hospital at 120 (1960).

G. R. Wilkinson, G. F. Peacock and E. L. Robins, "A Shorter Sterilizing Cycle for Solutions Heated in an Autoclave", 12 Supp. J. Pharm. Pharmacol. at 197T–202T (1960).

J. C. Kelsey, "The Testing of Sterilizers", 14 J. Clin. Path. at 313–319 (1961).

*Diack Sterilizer Control*, "Smith & Underwood" advertisement for Diack Controls, 96 Modern Hospital at 10 (1961).

G. R. Wilkinson and F. G. Peacock, "The Removal of Air During Autoclave Sterilization of Fabrics Using Low Pressure Steam", 13 J. Pharm. Pharmacol. Suppl. at 67T–71T (1961).

*Aseptic–Thermo Indicator Company (ATI)*, "Aseptic—Thermo Indicator Company", advertisement for Hi–Temp Indicators, 97 Modern Hospital at 116 (1961).

*Asptic–Thermo Indicator Company (ATI)*, "Aseptic—Thermo Indicator Company", advertisement for ATI Steriline Bags and Diack Controls, 97 Modern Hospital at 107 (1961).

G. R. Wilkinson and F. G. Peacock, "Improvement of Heating of Bottled Fluirds During Autoclave Sterilization Using Low Pressure Steam", 13 Supp. J. Pharm. Pharmacol. at 72T–74T (1961).

*Dennison Mgf. Co.*, "Dennison Manufacturing Company" advertisement for Dennison Wrap Autoclave Tape, 97(4) Modern Hospital at 233 (1961).

*Diack Sterilizer Controls*, "Smith & Underwood" advertsiement for Diack Controls, 98 Modern Hospital at 10 (1962).

*TSI Tape*, "Professional Tape Co., Inc." advertisement for TSI Tape, 98(3) Modern Hospital at 125 (1962).

G. R. Wilkison and F. G. Peacock, "Thermocouples for Autoclaves", 1 The Lancet at 488 (1962).

*ATI Steam–Clox*, "Aseptic-Thermo Indicator Company" advertisement for Steam–Clox Indicator", 40 Hospital Topics at 55 (1962).

*Sterilometer*, "Sterilometer Laboratories, Inc." advertisement for Sterilometer, 41(2) Hospital Topics at 74 (1963).

*Sterilometer*, "Sterilometer Laboratories, Inc." advertisement for Sterilometer, 1(2) AORN Journal at 86 (1963).

*Spordex*, "American Sterilizer" advertisement for Sporde–X Spore Strips, 100 Modern Hospital at 5 (1963).

*3M Autoclave Tape*, "Minnesota Mining and Manufacturing Company" advertisement for 3M Autoclave Tape, 100(5) Modern Hospital at 141 (1963).

*VAC Sterilizer Controls (Diack)*, "Diack Controls" advertisement for VAC Sterilizer Control, 101 Modern Hospital at 10 (1963).

J. H. Bowie, J. C. Kelsey and G. R. Thompson, "The Bowie and Dick" Autoclave Tape Test, 1 The Lancet at 586–587 (1963).

T. B. Owen, J. J. Perkins, A. S. Irons, A. W. Reichert and S. J. Mannarino, "Prevacuum High Temperature (List continued on next page.)

OTHER PUBLICATIONS

Steam Sterilization", 1 The Journal of Hospital Research, 5–30 (1963).

G. R. Wilkinson and L. C. Baker, "Modern Trends in Steam Sterilization", 5 Progr. Industr. Micro-Biol. at 231–282 (1964).

*Biospore Biological Sterility Indicators*, "Castle, Subsidiary of Ritter Company, Inc." advertisement for Spore Controls, 42(3) Hospital Topics at 13 (1964).

G. R. Wilkinson and L. C. Baker, "Contemporary Trends in Heat Sterilization", Advances in Pharm. Sci., vol. I, at 269–314 (1964).

G. R. Wilkinson and D. E. Simpkins, "A Physical Indicator for Sterilization Procedures", 16 Suppl. J. Pharm. Pharmacol. at 108T–110T (1964).

Sydney D. Rubbo and Joan F. Gardner, *A review of Sterilization and Disinfection*, Year Book Medical Publishers, Inc. at 6–65 (1965).

G. Sykes, *Disinfection and Sterilization*, 2nd Ed., J. B. Lippincott Company, at 121–145 (1965).

G. Sykes, *Disinfection and Sterilization*, 2nd Ed., "Methods of Sterilization" at 108–119 (1965).

J. C. Kelsey, "The Bowie-Dick Test", 2 The Lancet at 911–912 (1966).

Carl W. Lawrence and Seymour S. Block, "Sterilization by Heat", Disinfection, Sterilization and Preservation at 714–734 (1968).

I. J. Pflug, "Some Observation Regarding Factors Important in Dry Heat Sterilization", Cospar Technique Manual Number 4 at 51–58 (1968).

Thomas Laskaris and Albert L. Chaney, "Reliability of Biologic Autoclave Sterilization Indicators" 52(4) The American Journal of Clinical Pathology at 495–500 (1969).

Frances L. Clapp, "Panel Dicussion: Proposed Changes in the USP–Microbiological Aspects", 23 Bulletin of the Parenteral Drug Assoc. at 252–262 (1969).

Karl Kereluk and Robert S. Lloyd, "Ethylene Oxide Sterilization" (American Sterilizer Company), 7 The Journal of Hospital Research at 55–59 (1969), J. J. Perkins, "Principles and Methods of Sterilization", *Principles and Methods of Sterilization in Health Sciences*, 2nd Ed., selected pages, particlarly 488–493 (1969).

Charles Artandi, "Biological Indicators" (Ethicon, Inc.). 23 Bulletin Parenteral Drug. Assoc. at 254–257 (1969).

Larry Day, et al., "Panel Discussion: Biological Indicators—Manufacture and Quality Control for a Biological Indicator", *Bulletin Parenteral Drug Assoc.* (1970).

B. Litsky, "Studies on the Performance of Sterilizer Control Devices Under Experimental Conditions", Smith & Underwood (1970).

Wm. S. Miller, "Panel Discussion: Biological Indicators—(IV) Types of Biological Indicators Used in monitoring Sterilization Processes", 25 Bulletin of the Parenteral Drug Assoc. at 80–86 (1971).

Francis W. Bowman, "Panel Discussion: Biological Indicators—(III) Quality Control of Biological Indicators", 25 Bulletin of the Parenteral Drug Assoc. at 78–79 (1971).

Armand Marinaro, "Panel Discussion: Biological Indicators—(II) Development of a Biological Indicator Program", 25 Bulletin of The Parenteral Drug Assoc at 75–77 (1971).

John E. Doyle, "Sterility Indicator with Artificial Resistance to Ethylene Oxide", 25 Bulletin of the Parenteral Drug Assoc. at 98–104 (1971).

Irving J. Pflug, "Sterilization of Space Hardware"-(University of Minnesota), 1 Environmental Biology and Medicine at 63–81 (1971).

Arthur D. Little, Inc., "A Study of the Requirements, Preliminary Concepts and Feasibility of a New System to Process Medical/Surgical Supplies in the Field" (U.S. Army Medical Research and Development Command), National Technical Information Service, U.S. Department of Commerce, Report No. 72688 (1971).

Thomas Macek, "Some Thoughts on Sterilization and Sterility Control", 25(1) Bulletin of the Parenteral Drug Assoc. (1971).

Wm. A. Altemeier, "The Significance of Infection in Trauma", Scudder Oration on Trauma at 7–16 (1971).

J. K. Pickerill and R. Perera, "Air Detection in Dressings Steam Sterilizers", 20 Laboratory Practice at 406–413 (1971).

John J. Mayernik, "Biological Indicators for Steam Sterilization—A U.S.P. Collaborative Study", 26 Bulletin of the Parenteral Drug Assoc. at 205–211 (1972).

Robert F. Smith, "Quality Assurance in Hospital Steam Sterilization", Smith & Underwood Laboratories (1972).

I. J. Pflug, "Heat Sterilization", Industrial Sterilization at 239–281 (1972).

(List continued on next page.)

OTHER PUBLICATIONS

Thomas J. Macek, "Biological Indicators, A U.S.P. Review", 26(1) Bulletin of the Parenteral Drug Assoc. (1972).

S. Stanley Schneierson and edited by R. B. Roberts, "Sterilization by Heat", 10(2) Infections and Sterilization Problems at 67083 (1972).

H. P. Werner and Ch. Vutuc, "Die Eignung Von Chemischen Und Biologischen Indikatoren Zur Uberprufung Des Sterilisationeffektes Von Autoklaven" (Chemical and Biological Indicators for Monitoring Sterilization in Autoclaves), Zentralblatt at 561-568 (1972).

Rex O. Astrid and Zunino V. Hugo, "Chemical Monitors of Autoclave Sterilization (Translation), 100 Revista Medica De Chile at 1087-1090 (1972).

Propper Mgf., "Propper Sterilization Indicators", 24 Hospital Topics (1973).

Time Duo-Strip, "Professional Tape Company, Inc.", 73 Hospital Topics (1973).

Surgicot, Inc., "Sterilization Bag" advertisement, 3 Hospital Topics at 67 (1973).

W. A. Hennig, H. S. Stern, R. J. Laza and Y. S. Murthy, "Use of Bacillus stearothermophilus as a Biological Indicator", J. Bulletin of the Parenteral Drug Assoc. at 30-37 (1973).

D. Hugh Starkey and Clifton K. Himmelsback, "On the Avoidance of Failures in Sterilization", Hospitals at 143-152 (1974).

Frank B. Engley, "Discusses Sterilization, Disinfection, Antisepsis for Infection Control", Hospital Topics at 61-69 (1974).

Earle H. Spaulding, "Uses and Abuses of Disinfectants", 5 Hospital Topics at 7-8 (1974).

E. O. Indicators (ATI Company), "Performance Certified E. O. Indicators", Hospital Topics at 72 (1974).

C. W. Bruch, "Levels of Sterility Probabilities of Survivors vs. Biological Indicators", 28 Bulletin of the Parenteral Drug Assoc. at 105-121 (1974).

K. Kereluk and R. Gammon, "A Comparative Study of Bilogical Indicators for Steam Sterilization", 15 Developments in Industrial Microbiology at 411-416 (1974).

J. H. Bowie, "Bowie and Dick Test", I The Lancet at 1233 (1974).

Robert F. Smith, "Modified Bowie-Dick Test", I The Lancet at 1349 (1974).

Michael Korcynski, C. L. Peterson and C. C. Loshbaugh, "An Approach to Establishing Parenteral Solution Sterilization Cycles", 28 Bulletin of the Parenteral Drug Assoc. at 270-277 (1974).

Jan Hoborn, "Steam Sterilization: A Comparison of Steam-Clox and Some European Biological Indicators", 12 Health Laboratory Science at 225-229 (1975).

Diack and VAC Controls, "New Developments in EO Sterilization", 21(5) AORN Journal at 962 (1975).

Diack and VAC Controls, "Smith & Underwood" advertisement for Diack and VAC Controls, 21(2) AORN Journal (1975).

Four Autoclave Sterilization Indicators, "Aseptic—Thermo Indicator Company", 53 Hospital Topics at 42 (1975).

K. Kereluk, "Quality Control in Sterilization Procedures: Biological Indicators", 53 Hospital Topics at 25-39 (1975).

Irving J. Pflug, "Performance of Biological Indicators Designed for Monitoring", (1975).

Sybron/Castle, "UniSpore Biological Indicators", Castle/Sybron Service Bulletin at 1035 (1975).

John R. Gillis, "Biological Indicators for Steam Sterilization Process Monitoring", 29 Bulletin Parenteral Drug Assoc. at 111-121 (1975).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–17 is confirmed.

New claims 18–81 are added and determined to be patentable.

18. The indicator device according to claim 4 wherein the cover strip is polypropylene film.

19. The indicator device according to claim 1 wherein the cover strip is about 1 to 2 mils in thickness.

20. The indicator device according to claim 1 wherein the organic compound contains at least one functional group selected from the group consisting of ether, amide and hydroxy.

21. The indicator device according to claim 1 wherein the organic compound contains at least one function group selected from the group consisting of ether and amide.

22. The indicator according to claim 1 wherein the organic compound contains at least one functional group selected from the group consisting of hydroxy and amide.

23. The indicator according to claim 1 wherein the organic compound is salicylamide.

24. The indicator device according to claim 1 wherein the organic compound contains an amide group and an ether group.

25. The indicator device according to claim 20 wherein the amide group has the structural formula

wherein R is H or C, - C alkyl.

26. The indicator device according to claim 1 wherein the organic compound contains at least one oxygen or nitrogen atom.

27. A sterility indicator device for use in a steam autoclave to determine the presence of steam sterilization and to provide a visual response to the integrated time/temperature exposure to moist heat comprising:
(a) an aluminum foil backing strip;
(b) an organic compound having a normal melting point which is greater than a predetermined control temperature, said melting point being depressed below said control temperature by the absorption of water into said organic compound when said indicator device containing said organic compound is exposed to saturated water vapor at the control temperature, said control temperature being below the normal melting point of the organic compound, said organic compound containing at least one functional group selected from the group consisting of ether, amide and hydroxy; said organic compound being placed on said backing strip;
(c) a wicking means having one end of said wicking means in intimate contact with said compound, said wicking means extending away from said compound and being mounted on said backing strip; and
(d) a water vapor transmission rate controlling cover strip overlayer covering said compound and wicking means, said cover strip being bonded to said backing strip, said cover strip comprising polypropylene film of about 0.75 to about 3 mils in thickness;
said device being inoperative at the control temperature in the absence of water vapor and displaying a visual response of the integrated time/temperature exposure of a system to moist heat.

28. The indicator device according to claim 27 wherein the organic compound contain at least one functional group selected from the group consisting of hydroxy and amide.

29. The indicator according to claim 27 wherein the organic compounds contain at least one functional group selected from the group consistent of ether and amide.

30. The indicator device according to claim 27 wherein the organic compound is salicylamide.

31. The indicator device according to claim 27 wherein the organic compound contains an amide moiety having the structural formula

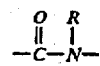

wherein R is H or C, - C, alkyl.

32. The indicator device according to claim 27 wherein the polypropylene film is about 1 to 2 mils in thickness.

33. The indicator device according to claim 27 wherein the wicking means is adhesively bonded to the backing strip.

34. The indicator device according to claim 27 wherein the cover strip is adhesively bonded to the backing stip.

35. The indicator device of claim 1 having a $Q_{10}$ response of from 18° F. to about 22° F.

36. The indicator device of claim 1 having a $Q_{10}$ response of about 18° F.

37. A sterility indicator device for use in a steam autoclave to determine the presence of steam sterilization and to provide a visual response to the integrated time/temperature exposure to moist heat, comprising:
(a) a backing strip comprising aluminum foil;
(b) an organic compound having a normal melting point which is greater than a predetermined control temperature, said melting point depressed below said control temperature by the absorption of water into said organic compound when said compound is exposed to saturated water vapor at the control temperature, said control temperature being below the normal melting point of the organic compound wherein said organic compound comprises salicylamide, said organic compound being placed on said backing strip;
(c) a wicking means having one end of said means in intimate contact with said compound, said wicking means comprising paper and extending away from said compound and being mounted on said backing strip; and
(d) a water vapor transmission rate controlling cover strip overlayer covering said compound and wicking means, said cover strip being bonded to said backing strip and being permeable to water vapor and having a water permeability coefficient at the control temperature such that sufficient water vapor will permeate the cover strip to reduce the melting point of the organic compound from its normal melting point to the control temperature, said vapor transmission rate controlling strip comprising polypropylene;

said device being inoperative at the predetermined control temperature in the absence of water vapor and displaying a visual response of the integrated time/temperature exposure of a system to moist heat, whereby the organic compound of the device, in the presence of moist heat at a temperature of at least the control temperature will migrate along the wicking means until at least a predetermined distance is reached, so that an indication is made of 100% spore kill level.

38. The indicator device of claim 37 wherein the polypropylene film is about 0.75 to about 3 mils thick.

39. The indicator device of claim 37 wherein the polypropylene film is about 1 to 2 mils thick.

40. The indicator device of claim 37 wherein the control temperature is about 250° F.

41. A sterility indicator for use in a steam autoclave to determine the presence of steam sterilization and to provide a visual response to the integrated time/temperature exposure of a material to be sterilized to moist heat, comprising:
  (a) a backing strip comprising aluminum foil;
  (b) an organic compound having a normal melting point which is greater than a predetermined control temperature, said melting point being depressed below said control temperature by the absorption of water into said organic compound when said compound is exposed to saturated water vapor at the control temperature, said control temperature being below the normal melting point of the organic compound, said organic compound containing ether and amide functional groups, said organic compound being placed on said backing strip;
  (c) a wicking means having one end of said means in intimate contact with said compound, said wicking means comprising paper and extending away from said compound and being mounted on said backing strip; and
  (d) a water vapor transmission rate controlling cover strip overlayer covering said compound and wicking means, said cover strip being bonded to said backing strip and being permeable to steam at the control temperature such that sufficient water vapor will permeate the cover strip to reduce the melting point of the organic compound from its normal melting point to the control temperature, said water vapor transmission rate controlling strip comprising polypropylene;

said device inoperative at the predetermined control temperature in the absence of water vapor and displaying a visual response of the integrated time/temperature exposure of a system to moist heat, whereby the organic compound of the device, in the presence of moist heat at a temperature of at least a predetermined distance is reached, so that an indication is made 100% spore kill level.

42. A sterility indicator device for use in a steam autoclave comprising:
  (a) a backing strip;
  (b) an organic compound having a normal melting point which is greater than a predetermined control temperature, said melting point being depressed below said control temperature by the absorption of water into said organic compound when said organic compound is exposed to water vapor at the control temperature, said organic compound containing at least one functional group selected from the group consisting of ether, amide and hydroxy, said organic compound being contained in a pocket embossed into the backing strip;
  (c) a wicking means having one end of said wicking means in intimate contact with said compound, said wicking means extending away from said compound and being mounted on said backing strip;
  (d) a water vapor transmission rate controlling cover strip overlayer covering said compound and wicking means, said cover strip being bonded to said backing strip and being permeable to steam at the control temperature such that sufficient water vapor will permeate the cover strip to reduce the melting point of the organic compound from its normal melting point to the control temperature;

said device being inoperative at the control temperature in the absence of water vapor and displaying a visual response of the integrated time/temperature exposure of a system to moist heat.

43. The indicator device according to claim 42 wherein the organic compound contains at least one functional group selected from the group consisting of hydroxy and amide.

44. The indicator device according to claim 42 wherein the organic compound contains at least one functional group selected from the group consisting of ether and amide.

45. The indicator device according to claim 42 wherein the organic compound contains an amide group and an ether group.

46. The indicator according to claim 42 wherein the cover strip is about 1 to 2 mils in thickness.

47. The indicator device according to claim 42 wherein the cover strip is polypropylene film.

48. The indicator device according to claim 47 wherein the polypropylene film is about 0.75 to about 3 mils thick.

49. The device according to claim 47 wherein the polypropylene film is about 1 to 2 mils thick.

50. The indicator device according to claim 42 where the control temperature is about 250° F. to 270° F.

51. The indicator device according to claim 42 wherein the wicking means is adhesively bonded to the backing strip.

52. The indicator device according to claim 42 wherein the cover strip is adhesively bonded to the backing strip.

53. The indicator device according to claim 42 having a $Q_{10}$ response of from about 18° F. to about 22° F.

54. The indicator device according to claim 42 having a $Q_{10}$ response of about 18° F.

55. The indicator device according to claim 42 wherein the organic compound is salicylamide.

56. The indicator device according to claim 42 wherein the backing strip comprises aluminum foil.

57. The indicator device according to claim 1 wherein the organic compound is contained in a pocket embossed into the backing strip.

58. The indicator device according to claim 1 wherein the water vapor rate controlling cover strip is about 0.75 to about 3 mils in thickness.

59. The sterility indicator device of claim 1 for use in a steam autoclave, wherein the visual response display includes a wicking distance representation, said representation being the wicking distance for a 100% spore kill level in said autoclave.

60. The sterility indicator device of claim 1 for use in a steam autoclave, wherein said visual response display includes a vertical line reltive to said wicking means showing the wicking distance required for 100% spore kill level in said autoclave.

61. The sterility indicator device of claim 27 for use in a steam autoclave, wherein the visual display includes a line relative to said wicking means showing the wicking distance required for 100% spore kill level in said autoclave.

62. The sterility indicator device of claim 27 for use in a steam autoclave, wherein the visual display includes a wicking distance representation, said representation being the wicking distance for a 100% spore kill level in said autoclave.

63. A sterility indicator device for use in a steam autoclave to determine the degree of steam sterilization at or above a predetermined control temperature and to provide a visual response to the integrated time/temperature exposure of a material to be sterilized to moist heat, comprising:
   (a) a foil backing strip;
   (b) an organic compound having a normal melting point which is greater than a predetermined control temperature, said melting point being depressible below said control temperature by the absorption of water into said organic compound when said indicator is exposed to saturated water vapor at the control termperature, said organic compound containing at least one functional group selected from the group consisting of ether, amide, and hydroxy, said organic compound being placed on said backing strip;
   (c) a wicking means having one end of said wicking means in intimate contact with said compound, said wicking means extending away from said compound and being mounted on said backing strip; and and
   (d) a water vapor transmission rate controlling cover strip overlayer covering said compound and wicking means, said cover strip comprising polypropylene film of about 0.75 to about 3 mils in thickness, said cover strip being bonded to said backing strip, said device being inoperative at the control temperature in the absence of water vapor and displaying a visual response to the integrated time/temperature exposure of said system to moist heat, said visual repsonse comprising a line perpendicular to the axis of said wicking means showing the wicking distance required for 100% spore kill level in said steam atmosphere.

64. The indicator device according to claim 63 wherein the organic compound contains at least one functional group selected from the group consisting of hydroxy and amide.

65. The indicator device according to claim 63 wherein the organic compound contains at least one functional group consisting of ether and amide.

66. The indicator device according to claim 63 wherein the organic compound contains an amide group and an ether group.

67. The indicator device according to claim 63 wherein the organic compound contains an amide group and a hydroxy group.

68. The indicator according to claim 63 wherein the cover strip is about 1 to 2 mils in thickness.

69. The indicator device according to claim 63 wherein the cover strip is polypropylene film.

70. The indicator device according to claim 68 wherein the cover strip consists of polypropylene film and is about 0.75 to about 3 mils thick.

71. The device according to claim 70 wherein the polypropylene film is about 1 to 2 mils thick.

72. The indicator device according to claim 63 wherein the control temperature is about 250° F. to 270° F.

73. The indicator device according to claim 63 having a $Q_{10}$ response of from about 18° F. to about 22° F.

74. The indicator device according to claim 63 having a $Q_{10}$ response of about 18° F.

75. The indicator device according to claim 63 wherein the organic compound is salicylamide.

76. The indicator device according to claim 63 wherein the backing strip comprises aluminum foil 77. The sterility indicator device for use in a steam autoclave to determine the degree of steam sterilization at or above a determined control temperature between about 250° F. to 270° F., said sterility indicator comprising:
   (a) an aluminum foil backing strip having a pocket or depression embossed therein;
   (b) an organic compound having a normal melting point about 5° F. to about 50° F. above the control temperature, the melting point of the organic compound being depressible below said control temperature by absorption of water into said organic compound when the compound is exposed to saturated water vapor at the control temperature, said organic compound containing at least one functional group selected from the group consisting of ether, amide and hydroxy, said compound being in said pocket or depression of said backing said compound containing a dye incorporated therein;
   (c) a wicking means comprising a filter strip placed on and aligned to the backing strip with a portion of one end in intimate contact with said pellet, said wicking means extending away from said compound;
   (d) a water vapor transmission rate controlling cover strip overlayer covering said compound and wicking means, said cover strip placed on and being bonded to said backing strip, said cover strip comprising a polypropylene film of about 0.75 to about 3 mils in thickness and being permeable to water vapor and having a water permeability coefficient at the control temperature such that sufficient water vapor will permeate the cover strip to reduce the melting point of the compound from its normal melting point to the control temperature, said device being inoperative at the control temperature in the absence of water vapor and displaying a visual response showing the wicking distance representing 100% spore kill level in said autoclave.

78. The sterility indicator device of claim 42 wherein said visual response display includes a line or representation relative to said wicking means showing the wicking distance required for 100% spore kill level in said autoclave.

79. The sterility indicator device of claim 77 wherein the organic compound has a normal melting point about 40° F. above the control temperature.

80. The sterility indicator device of claim 77 wherein the organic compound has a normal melting point at least about 20° F. above the control temperature.

81. A sterility indicator device for use in a steam autoclave to determine the degree of steam sterilization at or above a determined control temperature between about 250° F. to 270° F., said sterility indicator comprising:
   (a) an aluminum foil backing strip having a pocket or depression embossed therein;
   (b) an organic compound having a normal melting point greater than about 20°-30° F., above the control temperature, the melting point of the organic compound being depressible below said control temperature by absorption of water into said organic compound when the compound is exposed to saturated water vapor at the control temperature, said organic compound containing at least one functional group selected from the group consisting of ether, amide and hydroxy, said compound being in said pocket or depression of said backing, said compound comprising salicylamide and a dye incorporated therein;

(c) a wicking means comprising a paper strip aligned to the backing strip with a portion of one end in intimate contact with said pellet, said wicking means extending away from said compound;

(d) a water vapor transmission rate controlling cover strip overlayer covering said compound and wicking means, said cover strip being adhesively bonded to said backing strip, said cover strip comprising a polypropylene film of about 1-2 mils in thickness and being permeable to water vapor and having a water permeability coefficient at the control temperature such that sufficient water vapor will permeate the cover strip to reduce the melting point of the compound from its normal melting point to the control temperature, said device inoperative at the control temperature in the absence of water vapor and displaying a visual response comprising a vertical line showing the wicking distance representing 100% spore kill level in said autoclave.

* * * * *